United States Patent
McCormick et al.

(10) Patent No.: US 11,116,921 B2
(45) Date of Patent: Sep. 14, 2021

(54) INTEGRATED RAPID CHEMICAL DELIVERY SYSTEMS

(71) Applicants: Amy McCormick, Delray, FL (US); Kellen McCormick, Delray, FL (US)

(72) Inventors: Amy McCormick, Delray, FL (US); Kellen McCormick, Delray, FL (US)

(*) Notice: Subject to any disclaimer, the term of this patent is extended or adjusted under 35 U.S.C. 154(b) by 0 days.

(21) Appl. No.: 16/879,059

(22) Filed: May 20, 2020

(65) Prior Publication Data
US 2021/0046263 A1 Feb. 18, 2021

Related U.S. Application Data

(60) Provisional application No. 62/886,164, filed on Aug. 13, 2019.

(51) Int. Cl.
*A61M 15/08* (2006.01)
*H04M 1/02* (2006.01)

(52) U.S. Cl.
CPC ............ *A61M 15/08* (2013.01); *H04M 1/026* (2013.01)

(58) Field of Classification Search
CPC .................................................... A61M 15/08
See application file for complete search history.

(56) References Cited

U.S. PATENT DOCUMENTS

| | | | | |
|---|---|---|---|---|
| 5,730,118 A | * | 3/1998 | Hermanson | A45F 5/00 128/200.14 |
| 2003/0178023 A1 | * | 9/2003 | Harabin | A61M 15/00 128/200.24 |
| 2004/0108227 A1 | * | 6/2004 | Lotierzo | A44B 15/005 206/38.1 |
| 2014/0128132 A1 | * | 5/2014 | Cox, III | H04M 1/185 455/575.8 |
| 2015/0249478 A1 | * | 9/2015 | Greiner | B65D 85/70 455/575.8 |
| 2017/0292757 A1 | * | 10/2017 | Weaver | F25D 3/08 |
| 2019/0053612 A1 | * | 2/2019 | Santini | A45C 11/182 |

* cited by examiner

*Primary Examiner* — Olisa Anwah

(57) ABSTRACT

A rapid chemical delivery system is presented. The system includes a portable handheld chemical storage receiving receptacle, wherein the receptacle is configured to receive and mate with an insertable chemical container and wherein the container houses a chemical. The system also includes a base affixed to the chemical storage receptacle, wherein a side of the base is configured to connect with an object and another opposing side is configured to attach to the chemical storage receptacle. The system further includes a rapid chemical deployment mechanism utilizing the portable handheld chemical storage receptacle and arranged to deploy the chemical from the chemical container when activated.

16 Claims, 14 Drawing Sheets

INTEGRATED RAPID CHEMICAL DELIVERY SYSTEMS

RELATED APPLICATIONS

This application claims priority to U.S. Provisional Application No. 62/886,164 filed Aug. 13, 2019. The entire contents of the above application are hereby incorporated by reference as though fully set forth herein.

FIELD OF THE INVENTION

The present invention relates generally to chemical delivery systems, and more particularly, to integrated rapid chemical delivery systems, which utilize embedded chemical delivery systems incorporated into ubiquitous items in order to save lives.

BACKGROUND OF THE INVENTION

Many methods and systems have been used unsuccessfully attempting to incorporate lifesaving medications and chemicals into everyday items. Several devices and methods have been created attempting unsuccessfully to address the problem having the appropriate medication, anti-venom, and/or antidote at the ready to save lives in a practical way. These previous systems and methods have not been effective in solving the problem of people dying because the appropriate medication could not be delivered in a timely fashion. Further, these previous systems and methods have not been effective in taking advantage of technology and common everyday items to have the appropriate chemicals and/or medication available to save lives.

There have been many unsuccessful attempts by medical professionals to provide lifesaving medications in a manner that can be deployed quickly in order to save lives. Many of these ineffective methods and systems have been implemented but are not able to deliver medications because the medications are not readily disposable to be administered and/or the methods and systems used cannot rapidly and effectively deliver medications within time.

In the United States alone there are numerous people that die from chemical overdoses, critical physical conditions, insect and/or animal bites, because the appropriate chemicals could not be delivered quickly enough to counteract the drug and/or physical condition. In 2019, every 11 minutes someone in the U.S. dies from an opioid overdose. These deaths cause a burden on all of society.

Currently, $504 billion is the estimated total economic burden of the opioid crisis. These economic costs affect all United States taxpayers.

The Centers for Disease Control and Prevention has determined the aggregate "economic burden" of Opioid Use Disorder (OUD) in the United States alone to be nearly 80 billion USD annually, with regards to healthcare, addiction treatment and criminal justice costs, alongside the lost productivity and output among our nation's labor force. More importantly, over 130 individuals lose their lives to an opioid overdose on a daily basis throughout the United States.

As of 2017, the number of overdose deaths associated with both prescription and illicit opioids has quadrupled in the preceding 15 years and has doubled in the timespan of 2010 to 2016 alone. The number of deaths from overdose in 2015 alone was over 33,000, with that number rising to over 42,000 and 49,000 in 2016 and 2017, respectively. The United States has labeled the ongoing drug epidemic as a national public health emergency in October of 2017.

In 2018, there were 1,187 drug-related deaths in Scotland, a record and a staggering increase of 27 percent from the year before. Overdoses are more common in Scotland, by some measures more than even in the United States. Many of these deaths may have been prevented if the appropriate chemical delivery systems were available.

Aside from economic burdens and mortalities, opioid misuse also impacts productivity and output in the labor force. Workplaces that serve the public (ex: libraries, restaurants, parks) are more likely to witness visitors who overdose while onsite, and therefore these places lack the requisite chemicals to prevent deaths.

Most recently, in the United States, the inability to rapidly deliver medications that can counteract the effects of an opioid overdose has contributed to over 140 deaths per day.

Accordingly, there is an established need for chemical delivery systems which solve at least one of the aforementioned problems. Further, there is an established need for integrated rapid chemical delivery systems which can be incorporated in common areas, common devices, and/or items to provide a rapid chemical delivery system in order to save lives.

SUMMARY OF THE INVENTION

The present invention is directed to innovative integrated rapid chemical delivery systems. These systems are used to provide rapid chemical delivery in situations wherein time is of the essence for the chemicals to be administered. These systems incorporate chemical delivery mechanisms, activation devices, and/or chemical deployment systems into stationary and/or portable devices, components, systems, and/or other commonly used items in order to deploy lifesaving chemicals effectively and efficiently.

A rapid chemical delivery system is presented. The system includes a portable handheld chemical storage receiving receptacle, wherein the receptacle is configured to receive and mate with an insertable chemical container and wherein the container houses a chemical. The system also includes a base affixed to the chemical storage receptacle, wherein a side of the base is configured to connect with an object and another opposing side is configured to attach to the chemical storage receptacle. The system further includes a rapid chemical deployment mechanism utilizing the portable handheld chemical storage receptacle and arranged to deploy the chemical from the chemical container when activated.

In embodiments, the system can include a rapid chemical deployment mechanism which includes pushing through a membrane to puncture a seal.

In another embodiment, the system can include a rapid chemical deployment mechanism which includes utilizing a finger loop on the portable handheld chemical storage receptacle and at least a system user's thumb or finger.

In yet another embodiment, the system can include a base that is connected to the object with adhesive.

In an aspect, the system can include a base that is connected to the object with a quick-release Snap-on/Snap-off interface.

In another aspect, the system can also include a rapid chemical deployment mechanism which includes removal of the insertable chemical container from the receptacle prior to chemical delivery.

In yet another aspect, the system can also include a key chain, wherein the system is integrated onto the key chain configured to rapidly administer chemicals with a single action.

In an embodiment, the system can include chemicals which includes concentrations from about (0.4 mg/1 mL) to about (2 mg/2 mL).

In another embodiment, the system can also include a rapid chemical deployment mechanism which is a pop-out penetration device.

In yet another embodiment, the system can include a rapid chemical deployment mechanism which is a nasal inhaler.

In an aspect, the system can include a rapid chemical deployment mechanism which includes manual removal of the chemical container from the storage receptacle and wherein the chemical is deployed manually.

In another aspect, the system can also include a handheld chemical storage receptacle which includes an opening on a front end, the opening configured to allow a portion of the chemical storage container to protrude through the opening in order to deploy the chemical.

In yet another aspect, the system can include materials and thicknesses to provide protection of the chemical from exposure to temperature and sun radiation excursions.

In an embodiment, the system can include a rapid chemical deployment mechanism which includes other than removal of the insertable chemical container from the receptacle prior to chemical delivery.

In another embodiment, the system can also include a receptacle which includes a plurality of layers.

In an embodiment of the present invention, devices and systems can include, but are not limited to devices and/or systems that allows naloxone to be carried in a more convenient manner by both laypersons and health/safety professionals. Specifically, the system can be designed to attach to the back of a cellular phone and/or other mobile communication devices, and can include a compact, protective slot for a single, packaged unit of NARCAN®. The system can also include NARCAN® and/or other chemicals stored within cavities of covers and/or mobile devices.

In an embodiment, the system can include chemicals to address distinct subcategories of pain-relieving opioids to be addressed, such as, but not limited to natural, semi-synthetic, and synthetic.

In another embodiment, the system can also include other emergency product carriers such as but not limited to, EpiPen's, inhalers, naloxone injectables, "wallet" style phone casing with medication holder, glucose/diabetic supplies, and/or nitroglycerin (chest pain medications).

In another embodiment, the system can also be incorporated into a housing of a cell phone. The system can include pop-out inhalers, injectors, atomizers, and/or delivery devices which can be embedded into the casing of a mobile device, key chain, wallet, employee badge, and/or in a cell phone.

In yet another embodiment, the system can further be incorporated into a key chain. The key chain configured to rapidly administer chemicals with a single action.

In an aspect, the system can be incorporated into an employee badge. The employee badge configured to dispense chemicals with a push of a button.

In another aspect, the system can also be incorporated into a police body armor. The system can be configured to be deployed by law enforcement personnel with a push of a button.

In yet another aspect, the system can be incorporated into a doctor's or nurse's apparel. The apparel items can include eyeglasses, stethoscopes, medical scrubs, medical ID badges.

In an embodiment, the system can be incorporated into an automobile. The system can be embedded in a steering wheel of the automobile.

In another embodiment, the system can also be incorporated into a mobile device, such as but not limited to a tablet, laptop, and/or a smart device.

In yet another embodiment, the system can be incorporated into a writing instrument. The writing instrument configured with a chemical delivery system on an end of the instrument.

In an aspect, the system can be incorporated into a musical instrument. The musical instrument configured to deliver chemical upon an actuation action.

In another aspect, the system can be deployed without harm because if the cause of the unconsciousness is uncertain, giving naloxone is not likely to cause further harm to the person.

In yet another aspect, the system can include chemicals that may be injected in the muscle, vein or under the skin or sprayed into the nose. The chemical can be in concentrations including, but not limited to (0.4 mg/1 mL) and can be sprayed up the nose in concentrations including but not limited to (2 mg/2 mL).

According to an aspect of the present invention, a system suitable for use as a rapid chemical delivery system can be implemented in employee sections of retail stores, public and recreational facilities, restaurants, areas where homeless populations reside, for emergency response in accordance with good Samaritan laws and regulations. Further, embodiments of the present invention can be introduced via social media campaigns, and/or can be incorporated in a plurality of commonly used items.

In an embodiment, the system can include a data processor, computer, and/or algorithms. The system can further include biometric monitoring devices, including but not limited to a Fitbit, apple watches, emergency room monitoring equipment, and other health monitoring devices. Additionally, the system can include monitoring biometric values and can include mechanisms to deliver chemicals when biometric data being monitored indicates the need for chemicals to be administered.

In another embodiment, the system can include injection devices, nasal inhalers, pop-out penetration devices, and/or atomizing devices arranged to deliver chemicals.

In yet another embodiment, the system can include wearable devices, wherein the devices can be configured to administer chemicals upon an automatic or manual actuation.

In an aspect, the system can include a chemical storage receiving receptacle with a plurality of layers. The layers arranged such that environmental protection is provided for the chemical. The layers can include materials such as but not limited to rubber, silicon, synthetics, insulation layers, void areas, and/or coatings. The layers can be structured to provide protection from temperature, moisture, humidity, and/or sunlight radiation. The layers can include outer layers of various colors designed to provide radiative protection. The layers can include a plurality of thicknesses. In some embodiments, the system includes one layer.

In another aspect, the system can also include materials with a plurality of durometers of pliable and protective layers.

In yet another aspect, the system can include square spring loaded injectable chemical containers.

In an embodiment, the system can include nasal chemicals. In embodiments, the system can include injectable chemicals. In embodiments, the system can include aerosol chemicals. In embodiments, the system can include Narcan®.

In another embodiment, the system can also include activation mechanisms comprising removing the chemical storage device from the receptacle and manually delivering the chemical to a person.

In yet another embodiment, the system can include activation mechanism utilizing an opening in the receptacle allowing the application portion of the chemical delivery device to protrude through the opening and deploying the chemical to a person with a push or press of an activation device such as a seal puncture. In some embodiments, the chemical storage container is not removed from the receptacle during chemical delivery. In some embodiments, the chemical storage container is removed from the receptacle to deploy the chemical.

In an aspect, the system can include at least one blister pack.

In another aspect, the system can also include thicknesses of about 0.1 mm, 1 mm, 5 mm, 10 mm, 20 mm, 50 mm and/or any dimension in between.

In yet another aspect, the system can function as a chemical storage container, the container serving to protect the chemical while being stored.

These and other objects, features, and advantages of the present invention will become more apparent from the attached drawings and the detailed description of the preferred embodiments, which follow. It is understood, that the drawings are designed for the purposes of illustration and not as a definition of the limits of the embodiments of the present invention. It should be further understood that the drawings are not necessarily drawn to scale and are merely intended to conceptually illustrate the methods and systems described herein

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION

The following detailed description is exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
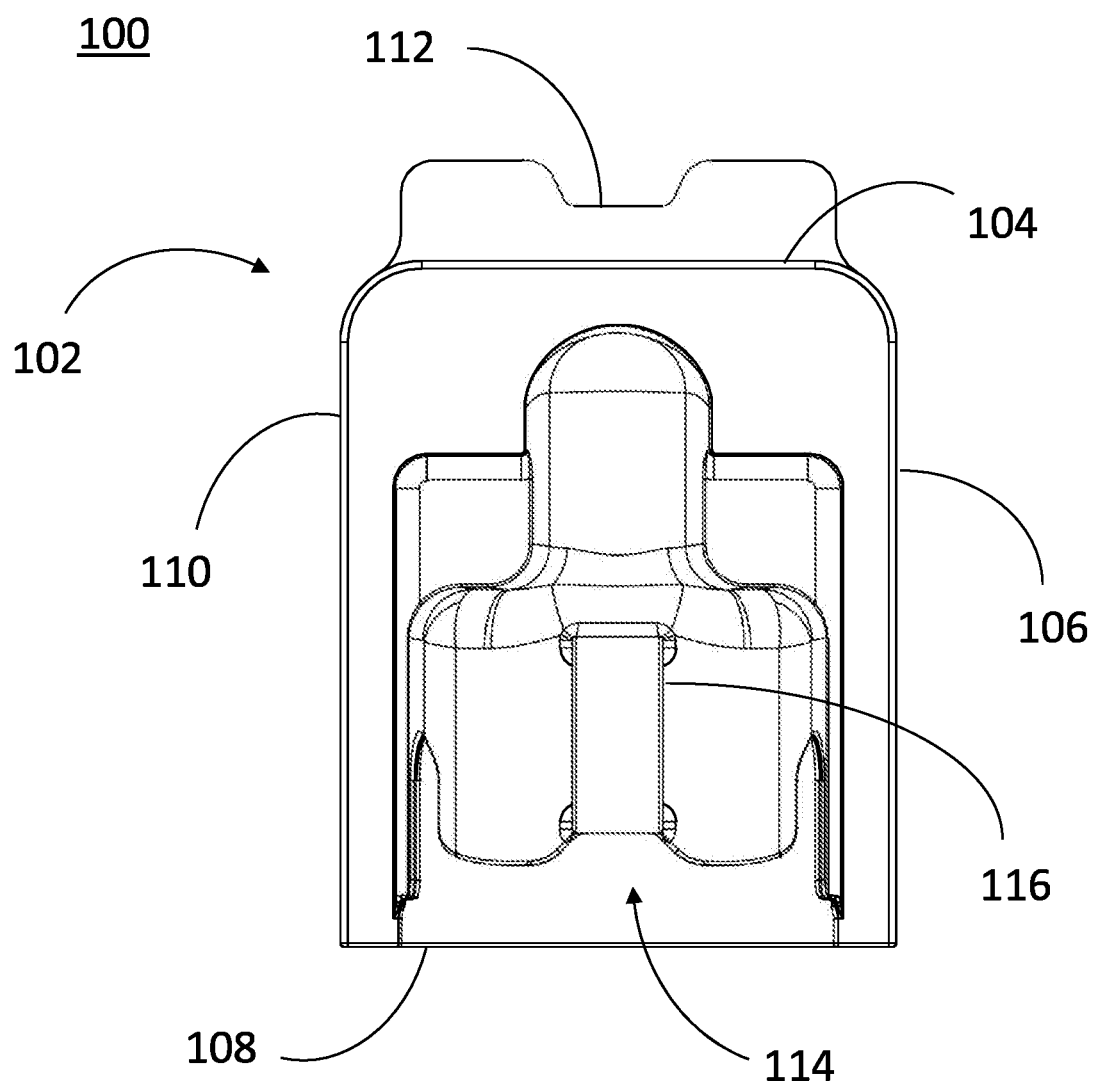
FIG. 1 presents a top view of an embodiment of a system incorporated in a cell phone holding device, in accordance with an embodiment of the present invention.

Referring initially to FIG. 1, a top view of an integrated rapid chemical delivery system 100 is displayed. As shown, an embodiment of the present invention can be incorporated in a cell phone holder 102. The cell phone holder 102 can include shapes such as but not limited to squares, rectangles, ovals, circles, and/or trapezoids. The shapes can be configured to allow a user of the cell phone holder improved handling and secure control for specific environments. The cell phone holder 102 can include a front side 104, a right-hand side 106, a back side 108, and a left-hand side 110 connected to form a contour of the cell phone holder 102. The system can also include credit card slots 112 for storing credit cards. The cell phone holder 102 can also include a chemical delivery system slot 114. In embodiments, the chemical delivery system slot can be arranged to accept and interface with Narcan® systems. Also, the system can include a finger loop 116 configured to provide users of the cell phone holder 102 positive control of the cell phone holder 102. Further, in embodiments not shown, the system can include incorporating a chemical delivery system on a back of cell phone and/or cell phone cover without a cell phone holder. Additionally, in embodiments not shown, the chemical delivery mechanism can be positionable within and/or on top of a cell phone cover. The cell phone cover can be structured to house and/or store chemicals and/or chemical delivery systems.

Figure 2:
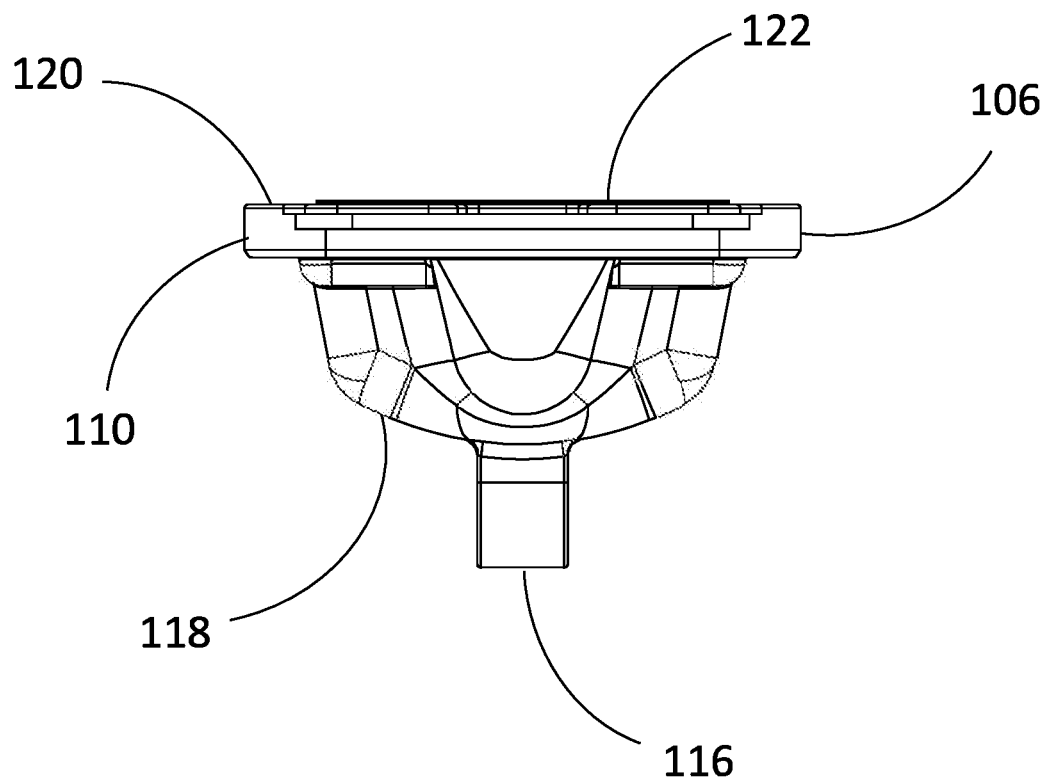
FIG. 2 presents an inverted front view of an embodiment of the system incorporated into a cell phone holding device.

FIG. 2 displays an inverted front view of a front side of a cell phone holder 102. The cell phone holder 102 can include a contoured top side 118. Further, the holder 102 can include a bottom side 120. The bottom side 120 contoured to mate with a cell phone and/or other mobile device. Additionally, the bottom side 120 can abut to a mating membrane 122, the membrane configured to allow connecting the bottom side 120 with the cell phone and/or mobile device. The membrane can include multiple layers and can also include shock absorbing features and/or adhesive features. In embodiments not shown the holder 102 can be affixed to other devices designed to be portable.

Figure 3:
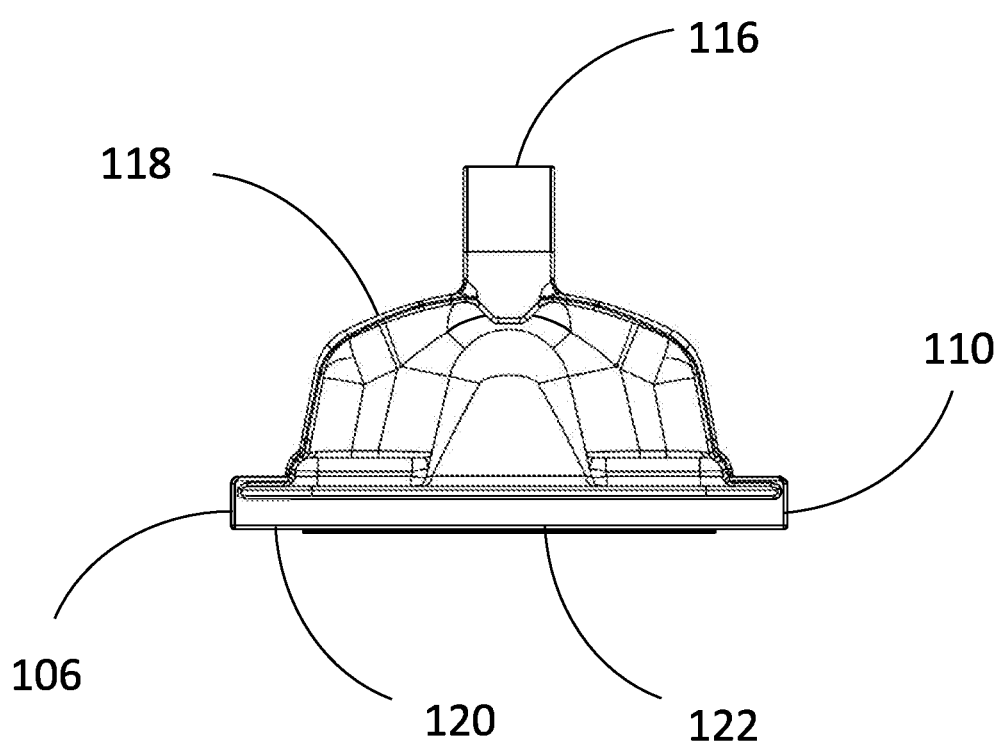
FIG. 3 presents a front view of an embodiment of the present invention on a cell phone holding device.

FIG. 3 is a view of a front side of a cell phone holder 102. The cell phone holder 102 can include a contoured top side 118. Further, the holder 102 can include a bottom side 120. The bottom side 120 contoured to mate with a cell phone and/or other mobile device. Additionally, the bottom side 120 can abut to a mating membrane 122.

Figure 4:
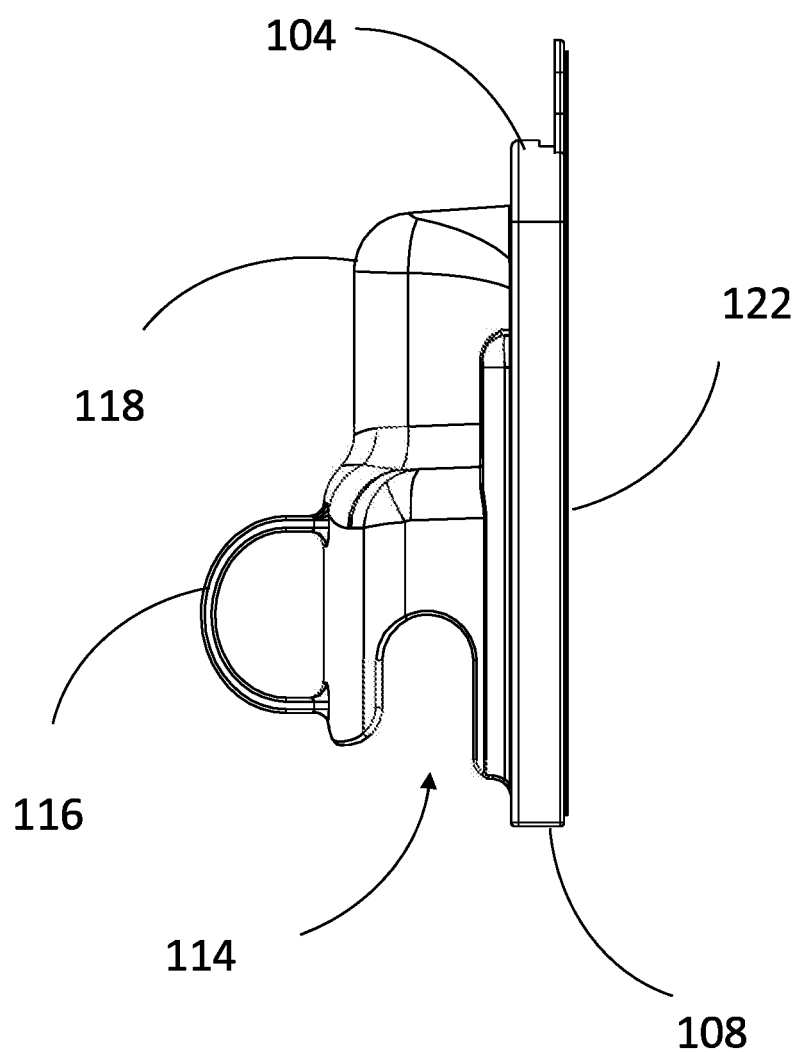
FIG. 4 presents a right-hand side view of a system incorporated on a side of a cell phone holding device in an embodiment of the present invention.

FIG. 4 is a right-hand side view of a cell phone holder 102. As best seen in FIG. 4, the holder 102 can include a chemical delivery system slot 114 configured for a plurality of chemical systems. Also, the system 100 can include a membrane 122 configured to abut to the bottom side 120 of the holder and arranged to provide an affixing interface between the bottom 120 of the holder 102 and a surface of a cell phone and/or a mobile device.

Figure 5:
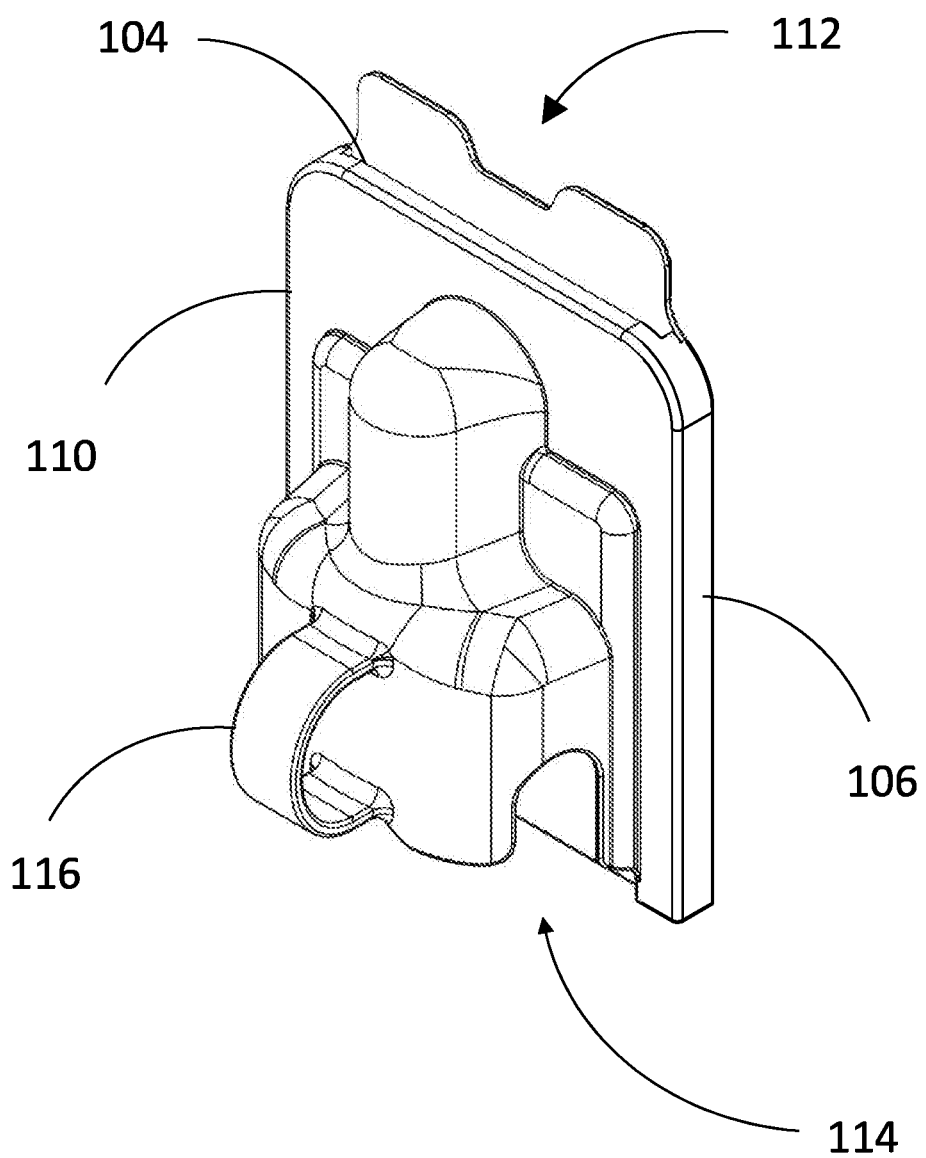
FIG. 5 presents top right-hand side perspective view of an embodiment of the present invention.

As best seen in FIG. 5, the system 100 can include a cell phone holder 102, the holder can also include credit card slots 112 arranged on a front side 104 of the holder 102. The credit card slots 112 can be structured to store one or a plurality of credit cards.

Figure 6:
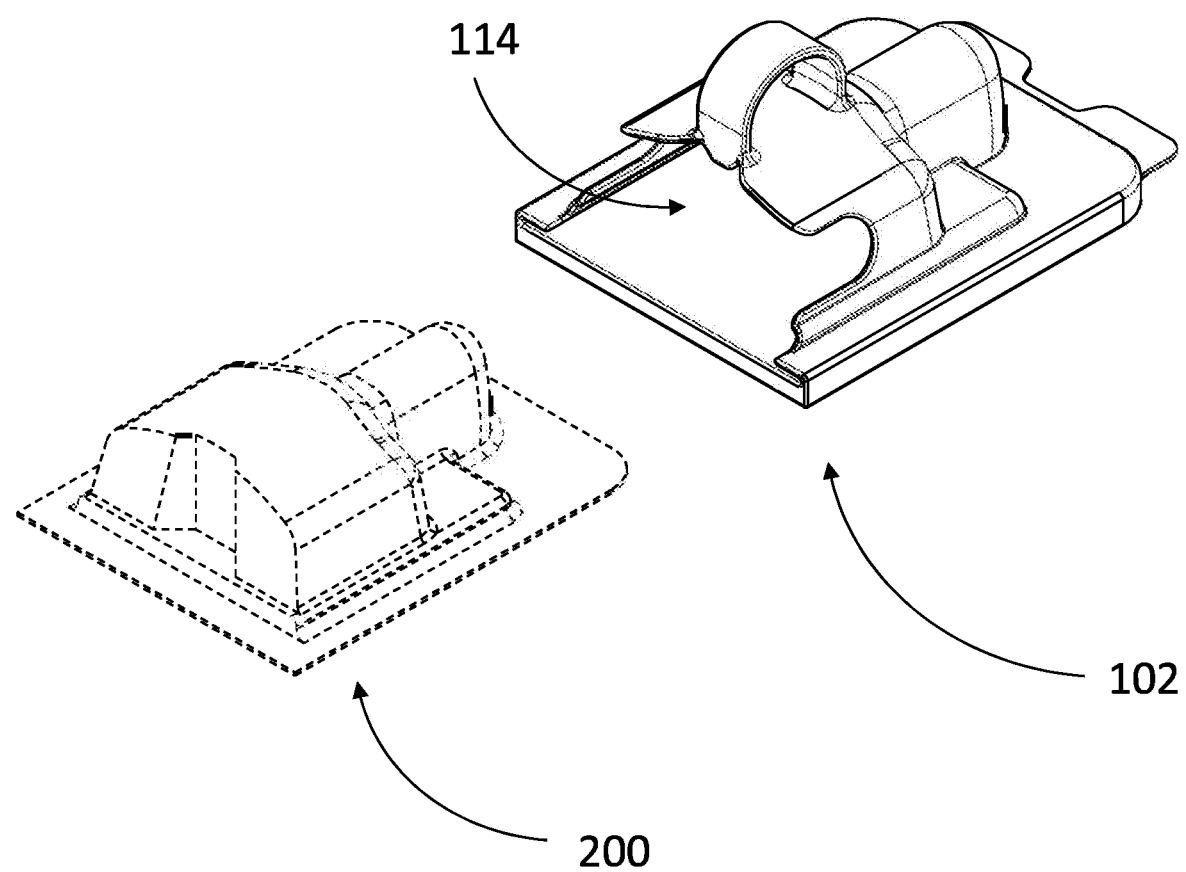
FIG. 6 presents a right-hand back side exploded view of a Narcan® injection system aligned with a cell phone holder in an embodiment of the present invention.

Referencing FIG. 6, an embodiment of the system 100 can be seen. As displayed an embodiment of a chemical delivery system 200 is aligned to mate with the cell phone holder 102 by coupling with the holder 102 in chemical delivery system slot 114. In some embodiments not shown, the slot 114 can be configured to mate with a plurality of chemical delivery systems, such as but not limited to Narcan®.

Figure 7:
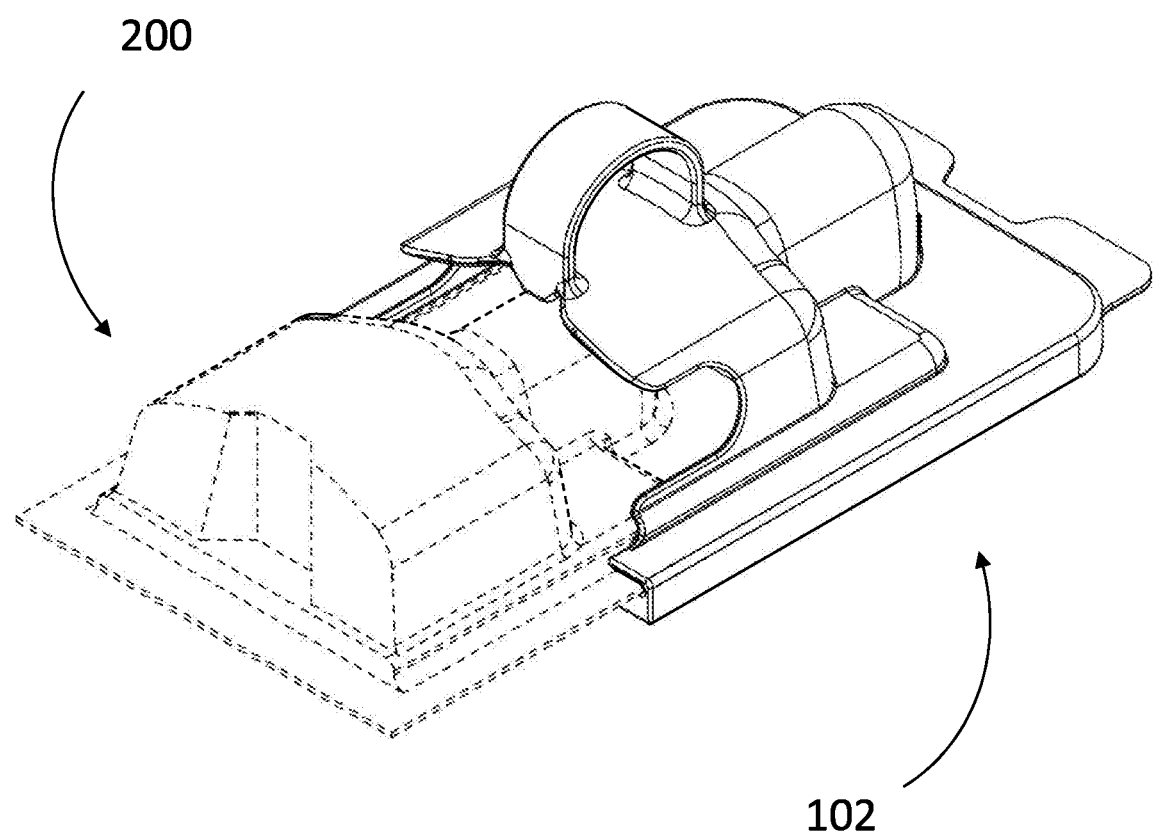
FIG. 7 presents a right-hand back side exploded view showing a Narcan® injection system being inserted into a cell phone holder in an embodiment of the present invention.

FIG. 7 illustrates a chemical delivery system 200 coupling with a cell phone holder 102 by mating with the chemical delivery system slot 114.

Figure 8:
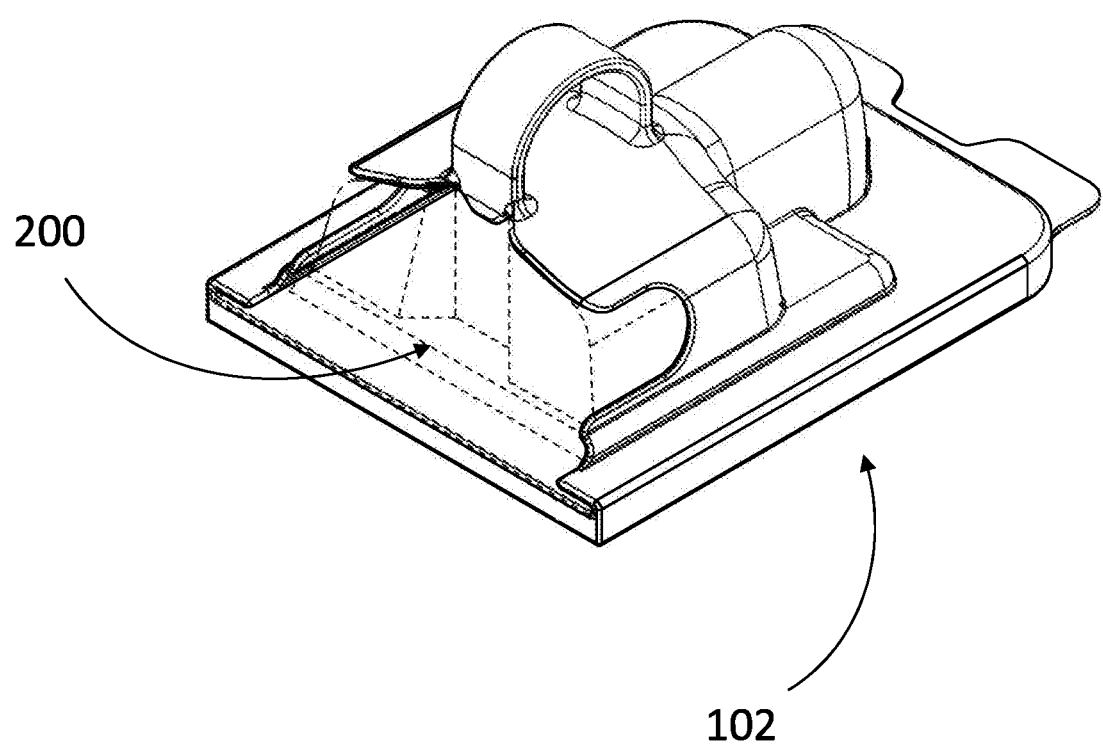
FIG. 8 presents a right-hand back side perspective view of an embodiment of the present invention with a Narcan® injection system inserted into a cell phone holder.

FIG. 8 shows a chemical delivery system 200 fully inserted into a cell phone holder 102.

Figure 9:
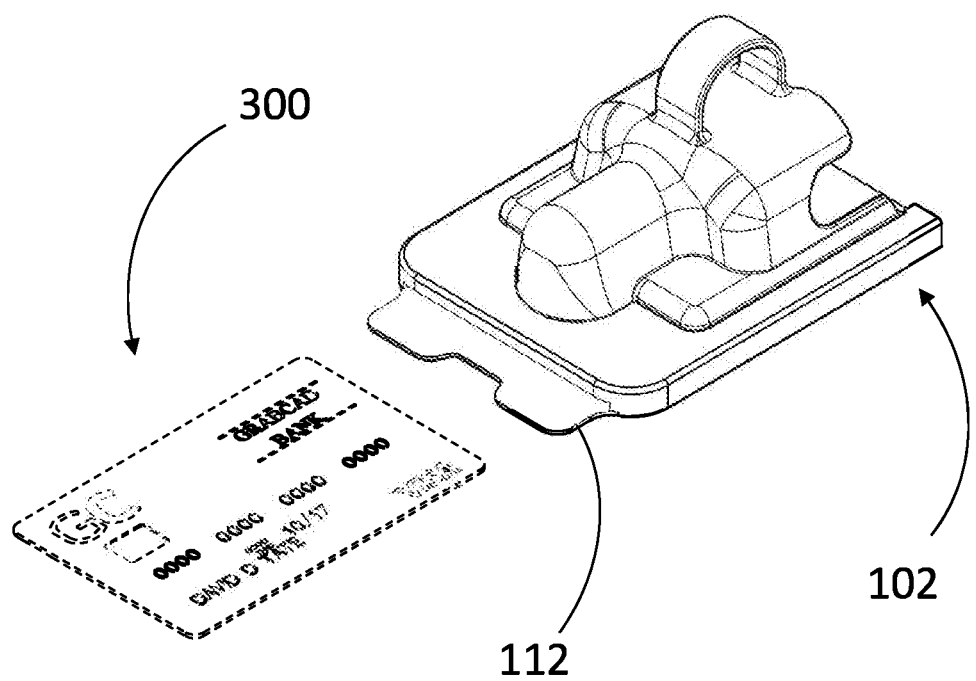
FIG. 9 presents a top left-hand side perspective exploded view of an embodiment of the present invention displaying a credit card aligned with a cell holder credit card slot.

As seen in FIG. 9, embodiments of the system include credit card slots 112 on a front side 104 of a cell phone holder 102 configured to receive and store credit cards 300. As shown in FIG. 9, a credit card 300 is aligned to enter into a credit card slot 112 of a cell phone holder 102.

Figure 10:
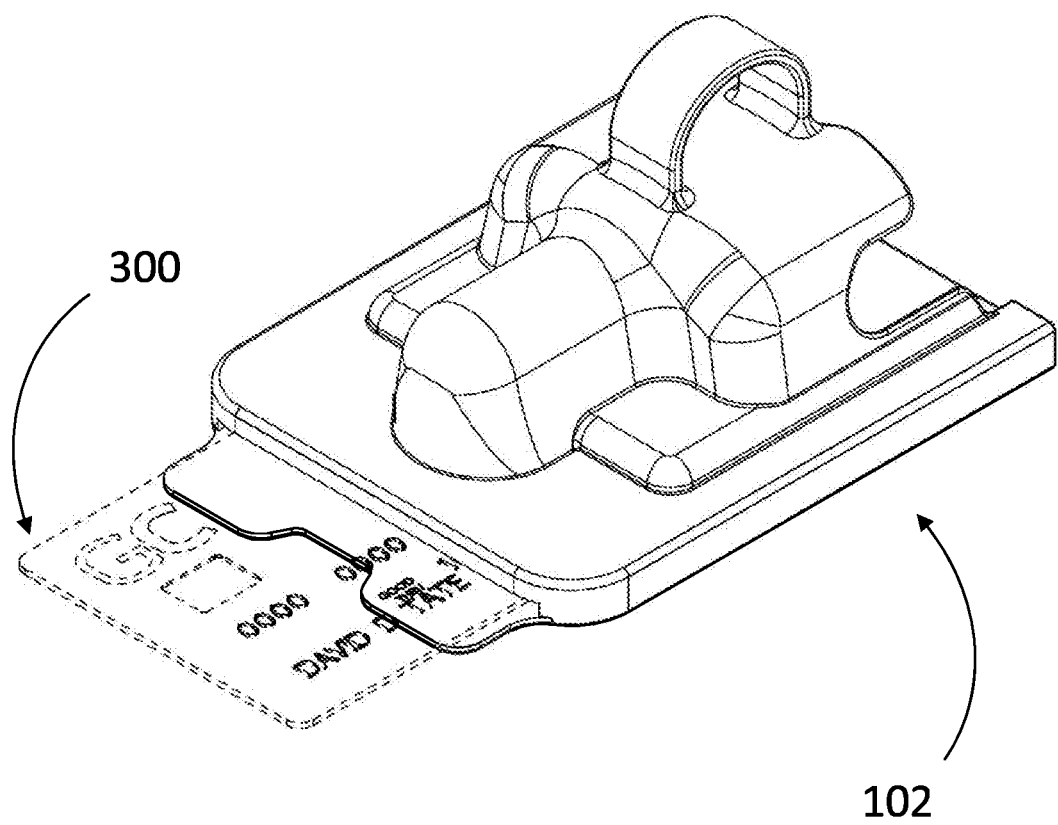
FIG. 10 presents a top left-hand side perspective exploded view showing a credit card being inserted into a credit card slot in a cell phone holder in an embodiment of the present invention.

FIG. 10 best shows how a credit card 300 enters into the credit card slot 112 on the cell phone holder 102.

Figure 11:
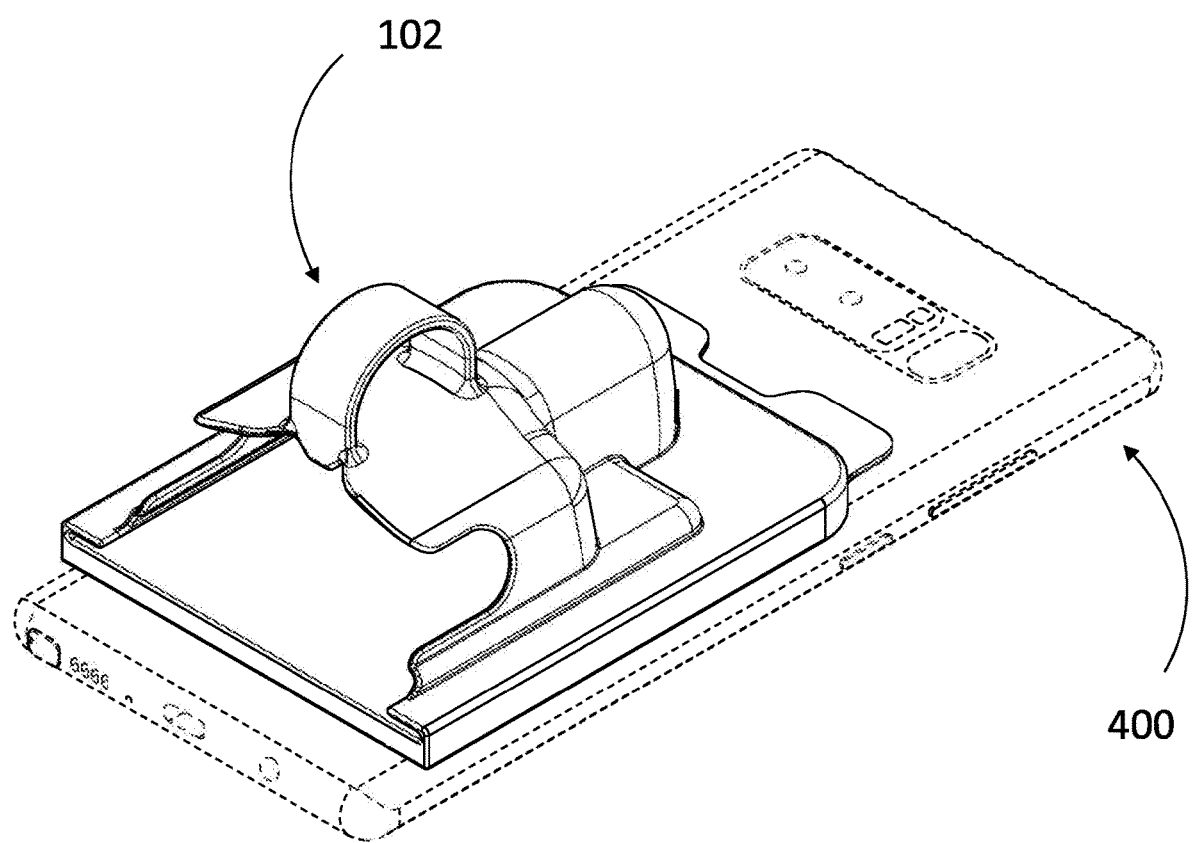
FIG. 11 presents a top right-hand side perspective back view of an embodiment of the present invention placed on a back of a cell phone.

Turning to FIG. 11, an embodiment of the present invention is shown attached to a cell phone 400. As seen in FIG. 11, a cell phone holder 102 is displayed affixed to a cell phone 400.

Figure 12:
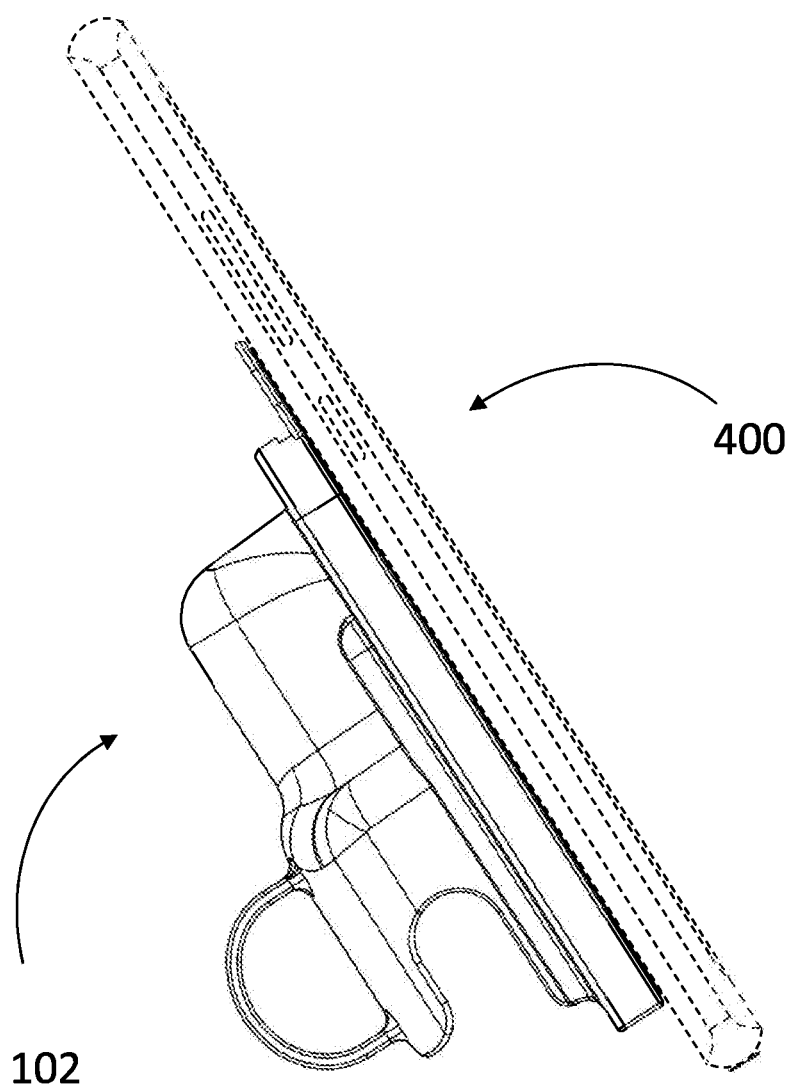
FIG. 12 presents oblique right-side view of an embodiment of the present invention connected with a cell phone.

Illustrated in FIG. 12 is an embodiment of the present invention showing that once a cell phone holder 102 is joined with a cell phone 400, maneuverability and vertical manipulation will not cause the cell phone holder 102 from disassociating from the cell phone 400.

Figure 13:
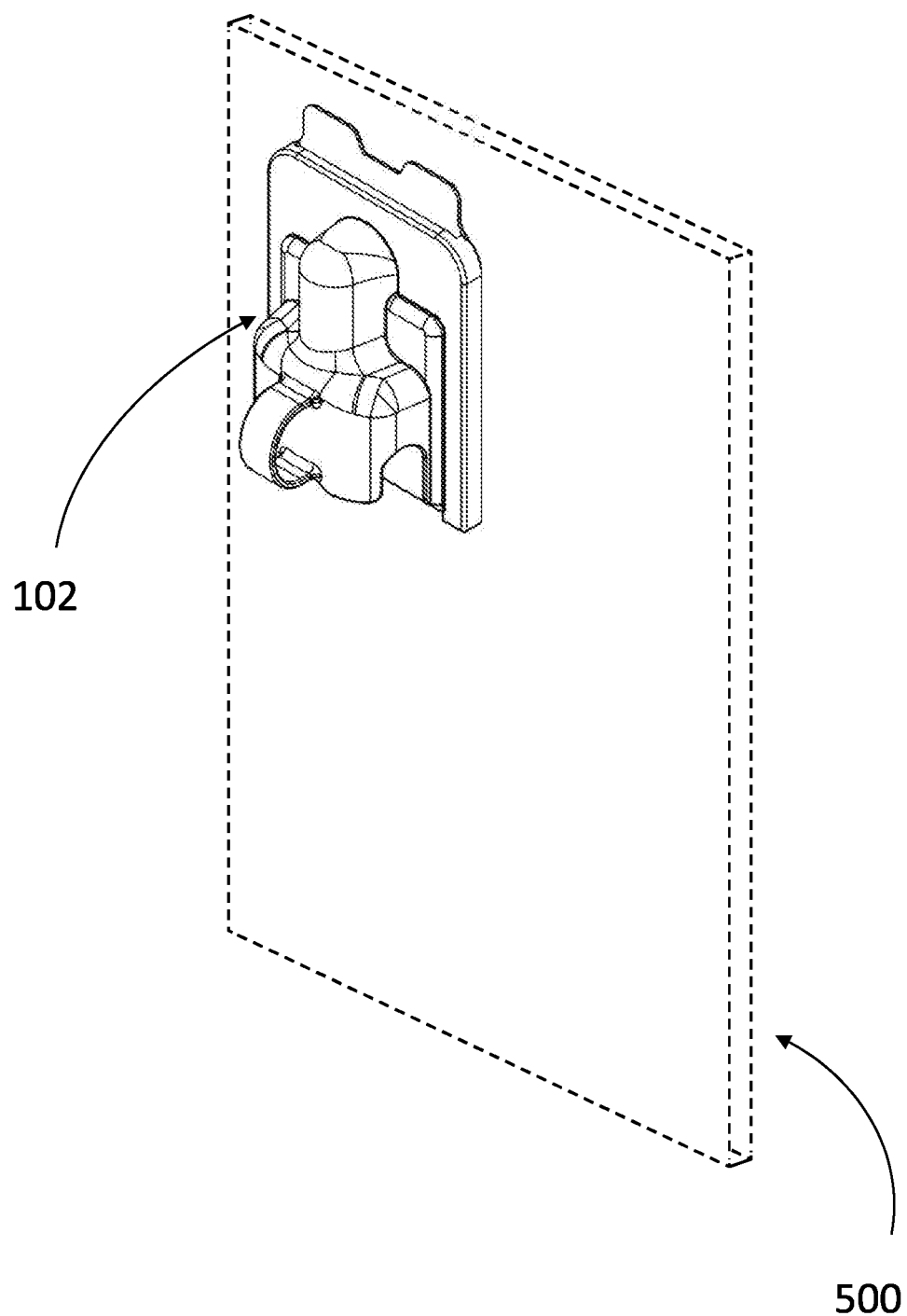
FIG. 13 presents a top front right-hand side perspective view of an embodiment of the present invention affixed to a flat surface.

FIG. 13 shows an embodiment of the present invention on a flat surface 500. The system 100 can be configured to be placed onto a flat surface horizontally, vertically and any angle in between. In the present embodiment a cell phone holder 102 interfaces with a flat surface 500.

Figure 14:
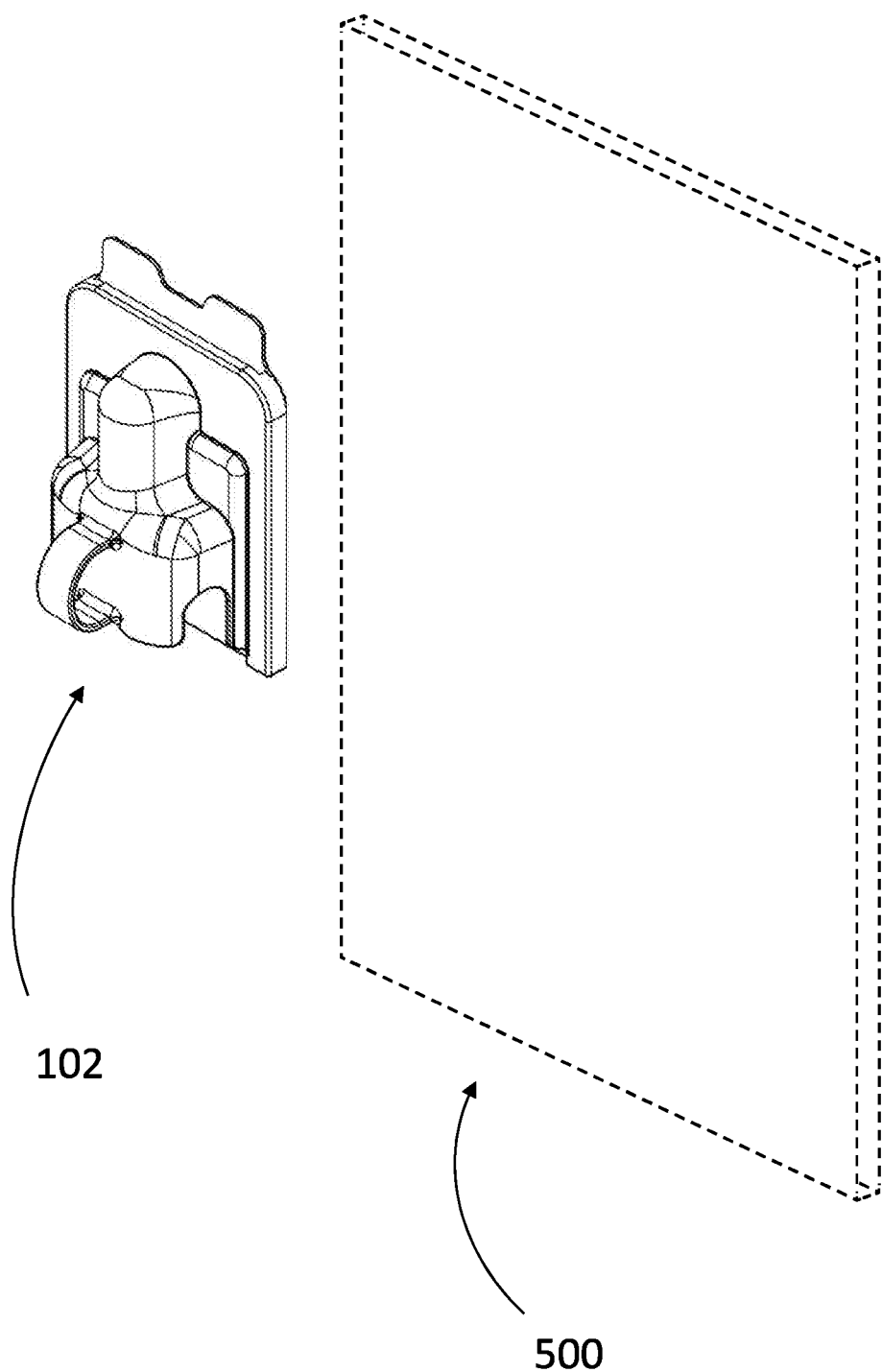
FIG. 14 presents a top front right-hand side perspective view of an embodiment of the present invention removed from a flat surface.

FIG. 14 displays disassociating of a cell phone holder 102 and a flat surface 500.

In embodiments, the system can include chemicals and chemical delivery systems incorporated on a back of a cellular telephone and/or back of a cellular telephone cover.

In embodiments not shown, the system can include everyday items and specialty items such as, but not limited to, keychains, garage door openers, security badges, FOB entry keys, police body armor, correction officer gear, medical staff identification badges, and/or college dorm residents' first aid kit. Embodiments can include chemicals and/or chemical delivery systems. Additionally, personnel assigned to monitor high risk demographics (half-way houses, recovery centers, treatment facilities, and/or support groups) can be provided embodiments of the present invention which are affixed to portable items for quick deployment.

Also, in embodiments not shown, the system can include chemicals and/or chemical delivery systems on a side of a cellular telephone. In embodiments not shown the system can include chemicals and/or chemical delivery systems on top, on a bottom, and/or within a cellular telephone, smart device, and/or mobile device.

In embodiments not shown, the system can include a cell phone stand. Wherein the stand can include chemicals and/or chemical delivery systems configured within the stand.

In embodiments not shown, the system can include a shoe. Wherein the shoe can include chemicals and/or chemical delivery systems configured within the shoe.

In embodiments not shown, the system can include heat resistant material. The materials arranged to protect chemicals and/or chemical delivery systems. The materials can include but not limited to, plastic, ceramic, metal, wood, composites, and/or fabric.

In embodiments not shown, the system can include adhesive material on a case and/or container of the medication such as but not limited Narcan®.

In embodiments, the system can include a loop for a finger to engage with a cell phone and medication on a back of the cell phone. The loop designed to handle a cell phone and/or administer chemicals.

In embodiments not shown, the system can be incorporated into a plurality of common everyday items. The system can include chemicals and/or chemical delivery systems that are positionable within cavities of the everyday items.

In embodiments not shown, the system can include biometric monitoring of high-risk personnel, the monitoring would provide an alert that biometrics are indicative of an overdose and/or need for immediate chemical delivery due to an imminent medical emergency. In embodiments the system can interface with smart watches and/or smart clothing to monitor recently recovering personnel or personnel who are required to wear location monitoring equipment. These embodiments would interface with automatic communication and alert systems to provide personnel to administer the required chemical and/or dispatch a robotic mechanism to deliver the chemical to the person who requires medication. The communications system utilized can use computers, data processors, software, and/or mobile applications to carry out functions.

In embodiments not shown, the system 100 can include cell phone holders 102 with finger loops 116 configured with movable components in order to allow induction charging of the cell phone 400.

In some embodiments, the method or methods described above may be executed or carried out by a computing system including a tangible computer-readable storage medium, also described herein as a storage machine, that holds machine-readable instructions executable by a logic machine (i.e. a processor or programmable control device) to provide, implement, perform, and/or enact the above described methods, processes and/or tasks. When such methods and processes are implemented, the state of the storage machine may be changed to hold different data. For example, the storage machine may include memory devices such as various hard disk drives, CD, flash drives, cloud storage, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API)

While the foregoing written description of the exemplary embodiments enables one of ordinary skill to make and use what is considered presently to be the best mode thereof, those of ordinary skill will understand and appreciate the existence of variations, combinations, and equivalents of the specific embodiment, method, and examples herein. The exemplary embodiments should therefore not be limited by the above described embodiment, method and examples, but all embodiments and methods within the scope and spirit of the exemplary embodiments as claimed.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

Insofar as the description above and the accompanying drawings disclose any additional subject matter that is not within the scope of the claims below, the inventions are not dedicated to the public and the right to file one or more applications to claim such additional inventions is reserved.

What is claimed is:

1. A rapid chemical delivery system comprising:
    a portable handheld chemical storage receiving receptacle, wherein the receptacle is configured to receive and mate with an insertable chemical container and wherein the container houses a chemical;
    a base affixed to the chemical storage receptacle, wherein a side of the base is configured to connect with an object and another opposing side is configured to attach to the chemical storage receptacle; and
    a rapid chemical deployment mechanism utilizing the portable handheld chemical storage receptacle and arranged to deploy the chemical from the chemical container when activated,
    a chemical delivery system slot configured within the chemical storage receiving receptacle, wherein the chemical delivery system slot includes a width of about 2.34 inches, a height of about 1.02 inches, a length of about 4 inches, and a protruding forward section with a width of about 0.98 inches; and
    a finger loop positioned on a top of the chemical delivery system slot, wherein the finger loop includes a width of about 0.47 inches, a length of about 0.87 inches, and a thickness of about 0.08 inches.

2. The system of claim 1 wherein the object is a cell phone.

3. The system of claim 1 wherein the rapid chemical deployment mechanism includes pushing through a membrane to puncture a seal.

4. The system of claim 1 wherein the rapid chemical deployment mechanism includes utilizing a finger loop on the portable handheld chemical storage receptacle and at least a system user's thumb or finger.

5. The system of claim 1 wherein the base is connected to the object with adhesive.

6. The system of claim 1 wherein the base is connected to the object with a quick-release Snap-on/Snap-off interface.

7. The system of claim 1 wherein the rapid chemical deployment mechanism includes removal of the insertable chemical container from the receptacle prior to chemical delivery.

8. The system of claim 1 further comprising a key chain, wherein the system is integrated onto the key chain configured to rapidly administer chemicals with a single action.

9. The system of claim 1 wherein the chemical includes concentrations from about (0.4 mg/1 mL) to about (2 mg/2 mL).

10. The system of claim 1 wherein the rapid chemical deployment mechanism is a pop-out penetration device.

11. The system of claim 1 wherein the rapid chemical deployment mechanism is a nasal inhaler.

12. The system of claim 1 wherein the rapid chemical deployment mechanism includes manual removal of the chemical container from the storage receptacle and wherein the chemical is deployed manually.

13. The system of claim 1 wherein the handheld chemical storage receptacle includes an opening on a front end, the opening configured to allow a portion of the chemical storage container to protrude through the opening in order to deploy the chemical.

14. The system of claim 1 wherein the system includes materials and thicknesses to provide protection of the chemical from exposure to temperature and sun radiation excursions.

15. The system of claim 1 wherein the rapid chemical deployment mechanism includes other than removal of the insertable chemical container from the receptacle prior to chemical delivery.

16. The system of claim 1 wherein the receptacle includes a plurality of layers.

* * * * *